United States Patent [19]

Nelson et al.

[11] Patent Number: 4,874,572

[45] Date of Patent: Oct. 17, 1989

[54] METHOD OF AND APPARATUS FOR MEASURING VAPOR DENSITY

[75] Inventors: Loren D. Nelson, Morrison; Todd A. Cerni, Littleton, both of Colo.

[73] Assignee: Ophir Corporation, Colo.

[21] Appl. No.: 46,286

[22] Filed: May 6, 1987

[51] Int. Cl.$^4$ .......................... G21C 17/00; G01J 1/00
[52] U.S. Cl. .................................. 376/256; 250/339; 250/343
[58] Field of Search ................ 376/256, 245; 250/339, 250/343; 73/336.5, 29, 265

[56] References Cited

U.S. PATENT DOCUMENTS

| | | | |
|---|---|---|---|
| 3,636,768 | 1/1972 | Tinet et al. | 73/336.5 |
| 3,820,398 | 6/1974 | Rekai | 73/336.5 |
| 3,860,818 | 1/1975 | Stalder et al. | 250/343 |
| 4,083,249 | 4/1978 | Gerber | 73/336.5 |
| 4,087,690 | 5/1978 | Probes | 250/343 |
| 4,291,323 | 9/1981 | Bachmann | 250/211 J |
| 4,394,575 | 7/1983 | Nelson | 250/343 |
| 4,481,417 | 11/1984 | Inglee | 250/338.1 |
| 4,520,265 | 5/1985 | Griggs et al. | 250/343 |
| 4,679,063 | 7/1987 | White | 250/338.4 |
| 4,785,170 | 11/1988 | Witt | 250/226 |

OTHER PUBLICATIONS

L. D. Nelson, "Non-Contact Sensing of Atmospheric Temperature, Humidity, & Supersaturation", American Meterological Society-Preprints Volume for Conference on Cloud Physics, (Chicago, IL, Nov. 15–18, 1982).

*Primary Examiner*—Harvey E. Behrend
*Assistant Examiner*—Daniel Wasil
*Attorney, Agent, or Firm*—Rothgerber, Appel, Powers & Johnson

[57] ABSTRACT

Apparatus and method determine the concentration of an individual component, such as water vapor, of a multi-component mixture, such as a gaseous mixture for cooling a nuclear reactor. A hygrometer apparatus includes an infrared source for producing a broadband infrared energy beam that includes a strong water vapor absorption band and a weak water vapor absorption region. The beam is chopped to select infrared pulses. A temporally first pulse has a wavelength in the weakly absorbing region, a temporally second pulse has a wavelength in the strong band and a temporally third pulse has a wavlength in the weakly absorbing region. A fourth reference pulse representing background radiation is interposed in such chopped pulses. An indium arsenide infrared sensor is responsive to the pulses for generating an output signal in proportion to:

$$\frac{N1 - N4}{[K2(N2 - N4) + K3(N3 - N4)]},$$

where N1 is proportional to the transmission through the sample of the first signal, N4 is related to the background radiation, and [K2 (N2−N4)+K3 (N3−N4)] is the time-weighted average of the transmission through the sample of the second and third pulses applicable at the time of the second pulse, with the reference pulse N4 being subtracted in each case to render the ratio independent of variations in the background radiation.

32 Claims, 3 Drawing Sheets

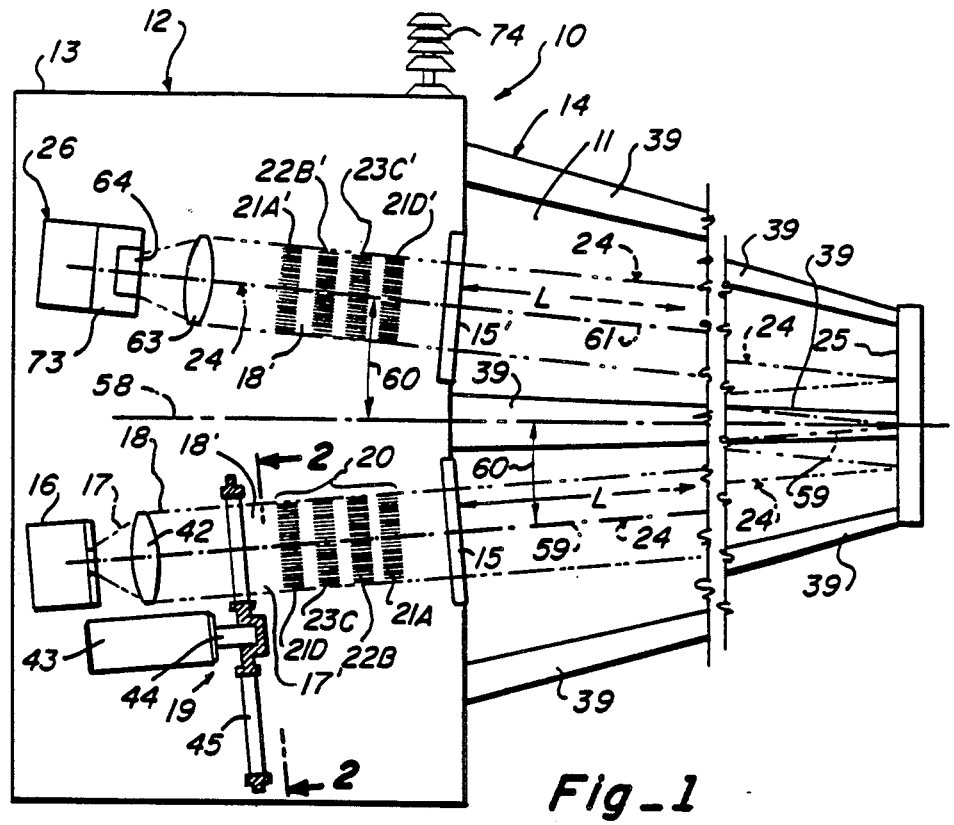
Fig_1
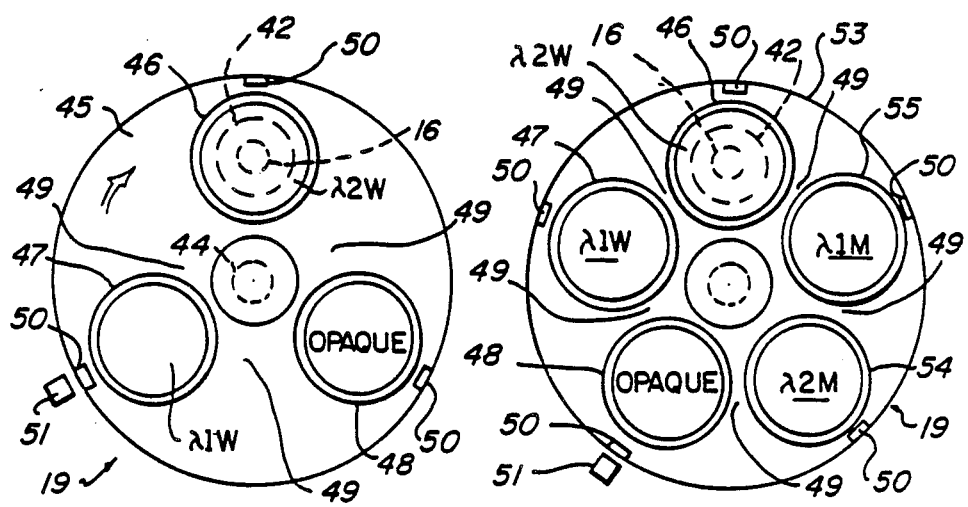
Fig_2A  Fig_2B

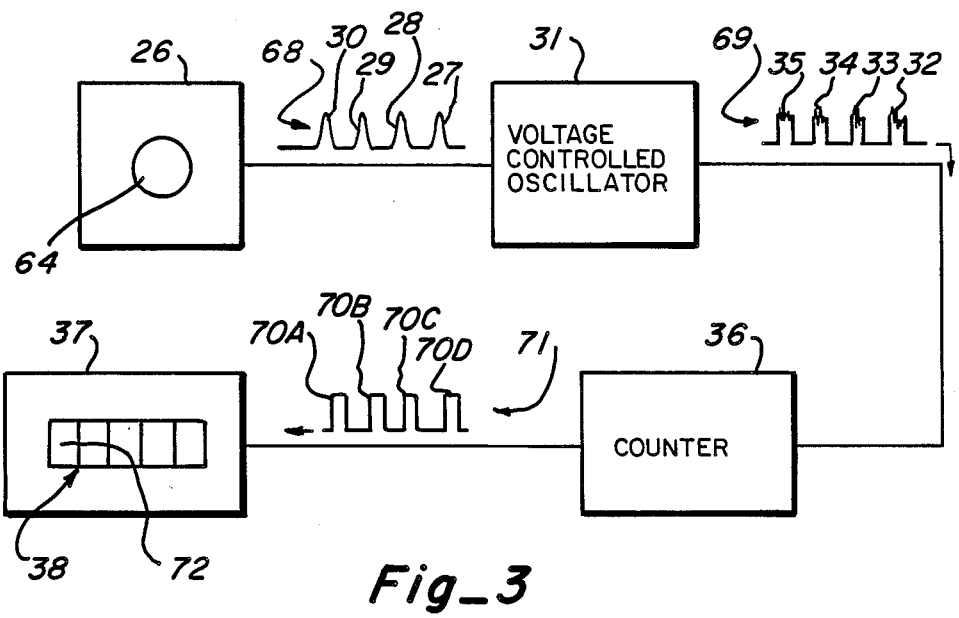
Fig_3
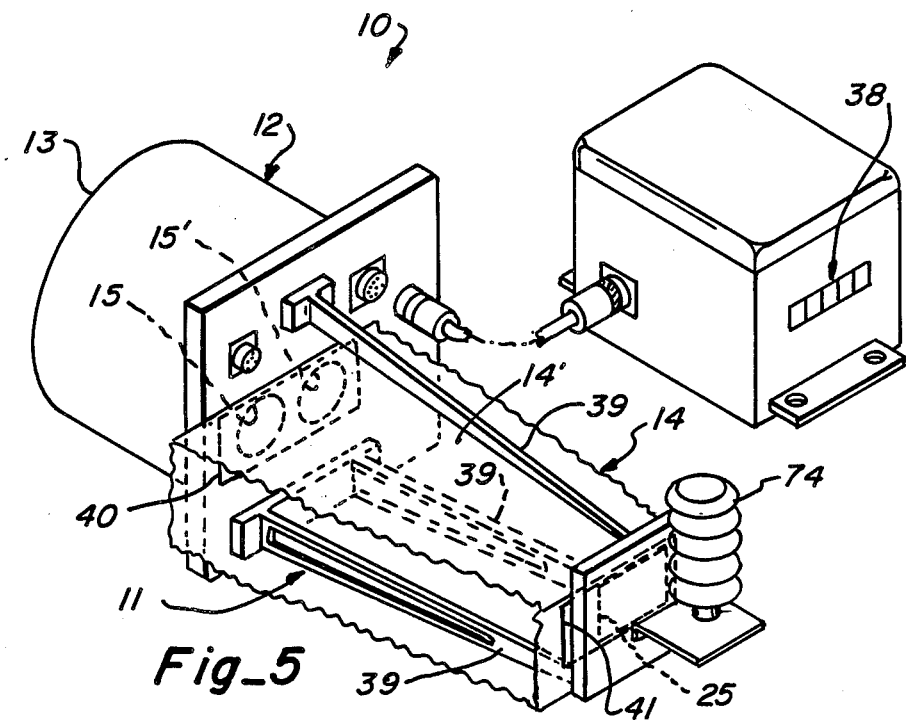
Fig_5

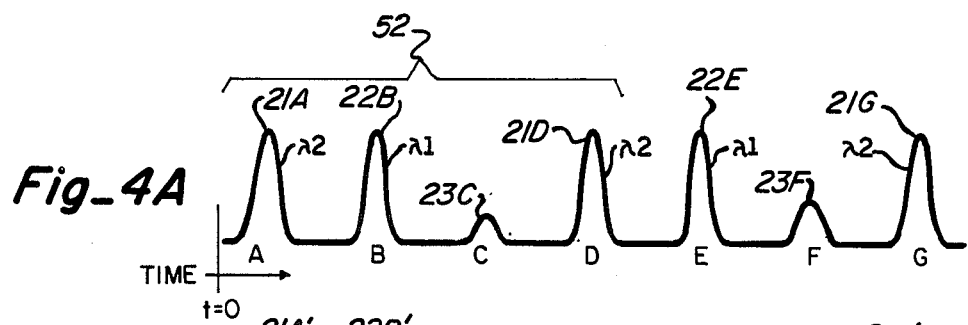
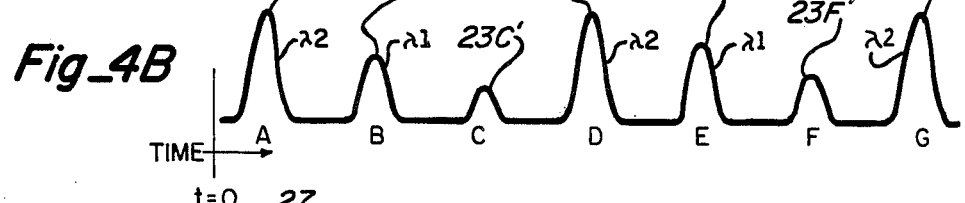
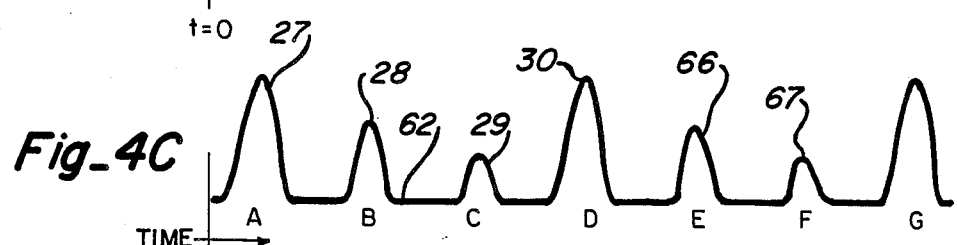
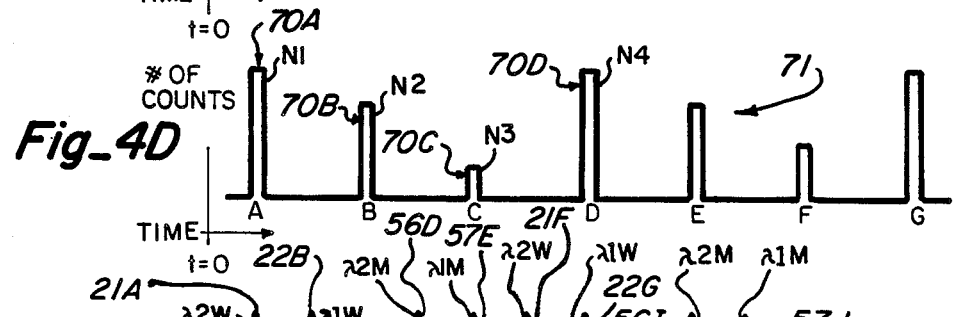
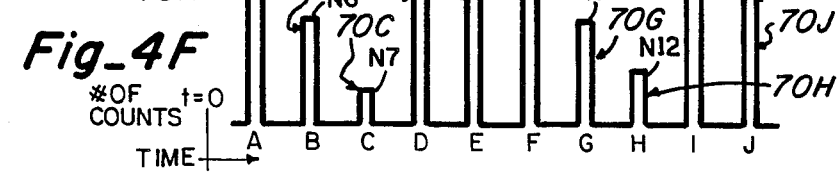

METHOD OF AND APPARATUS FOR MEASURING VAPOR DENSITY

RIGHTS TO INVENTION

This invention was made with Government support under Contract No. DE-AC03-83ER 80090 awarded by the Department of Energy. The Government has certain rights in this invention.

BACKGROUND OF THE INVENTION

1 Field of the Invention

The present invention relates to the field of measuring the concentration of individual components of a multi-component system and more particularly to the use of gaseous absorption spectroscopy to measure gaseous component vapor densities in samples that may contain aerosols and that may be supersaturated in the sampled component or other gases.

2 Description of the Prior Art

Multi-component systems may be composed of air plus other gaseous components, such as carbon dioxide, methane or water vapor, for example. Since 1912, when F. E. Fowle described a spectroscopic means of determining the ambient concentration of aqueous vapor, efforts have been made to improve upon the accuracy of hygrometers, which measure the concentration of the component water vapor in air. Such efforts have also attempted to extend the effective operating life of hygrometers independently of conditions encountered in the field.

An ideal instrument for measuring the concentration of a component of a multi-component system must be able to withstand harsh environmental conditions without loss of functional efficiency, permit maintenance without disassembly of the instrument, have long intervals between required maintenance, have low operational power requirements, and have an electromagnetic radiation sensing element that has stable and repeatable response characteristics. Despite the efforts since Fowle's work to develop such instruments in the form of hygrometers, until the present invention, such instruments having all of the above ideal characteristics have not been developed.

Photoconductive infrared sensors have been used in the past for measuring vapor density by gaseous absorption spectroscopy. However, the response of photoconductors to incident radiation is inherently non-linear. Since saturation of the sensor occurs as the intensity of the radiation increases, as such saturation occurs the photoconductor output levels off even though increased radiation intensity is directed onto the photoconductor.

The conductivity of a photoconductive sensor is increased by heating and by incident radiation. To reliably relate variable conductivity of the photoconductive sensor to variable conditions in the volume of the system being sampled at any instant, the photoconductor and its optically viewed background must be maintained at a constant temperature. In existing designs that maintain the entire instrument at a constant temperature, such temperature control requires about 200 watts of operating power and requires a warm up period of about 30 minutes. The non-linearity characteristic and the temperature control requirements have substantially increased the difficulty encountered in attempting to design an ideal instrument for measuring the concentration of individual components of a multi-component system using photoconductive sensors.

In L. D. Nelson U.S. Pat. No. 4,394,575, filed June 30, 1980, issued July 19, 1983 for APPARATUS FOR MEASURING VAPOR DENSITY, GAS TEMPERATURE, AND SATURATION RATIO, a lead selenide photoconductor for measuring gas temperature was disclosed. In that Patent, mention was made that other sensors capable of detecting infrared radiation such as, for example, bolometers or photoconductors or photovoltaic cells of other materials could be substituted for the lead selenide photoconductor without changing the instrument or method of measuring gas temperature. Although reference was there made to photovoltaic cells for gas temperature measurements, in 1980 relatively little was known about the application of photovoltaic cells in optical instruments for measuring vapor density.

Apart from the limitations presented by photoconductive sensors, other efforts have been directed to improving the structure of hygrometers. For example, an infrared source has been used to produce two identical beams which are alternately intercepted and directed through separate chambers. In such system, a first chamber through which the first beam is transmitted must be maintained in a dry condition to act as a reference. The other chamber through which the other beam is transmitted is provided with water vapor-bearing atmosphere to be measured. In such system, the difference in the intensities of the separate beams that are transmitted through the separate enclosures is used to indicate humidity in the ambient chamber. The accuracy of such system is dependent upon maintaining a constant dry condition in the reference chamber.

Attempts have been made to compensate for the non-linearity of photoconductors by using relatively complicated circuitry. One example is disclosed in A. Rekai U.S. Pat. No. 3,820,398 issued July 28, 1974 for "System for Providing a Linear Output from a Non-Linear Condition Responsive Device". The provision of such complex compensating circuitry is to be avoided in the ideal instrument for measuring the concentration of individual components of a multi-component system.

SUMMARY OF THE INVENTION

In contrast to the prior art in which non-linear electromagnetic radiation sensors were used and were compensated for by complex circuitry, and in which dry reference chambers were maintained for comparison with ambient conditions, the present invention provides a method and apparatus for measuring the concentration of individual components of a multi-component system by directing electromagnetic radiation in a single path through a sample and onto a photovoltaic sensor having linear response characteristics.

A method and apparatus according to the present invention utilizes a photovoltaic sensor for response to infrared energy having a first wavelength that is strongly absorbed by a selected gaseous component, such as carbon dioxide or methane or water vapor, for example, and having a second wavelength that is weakly absorbed by such component, wherein such infrared energy is transmitted through a sample in the form of pulses having such first and second wavelengths.

Apparatus designed in accordance with the principles of the present invention is provided with an indium arsenide sensor for response to a series of pulses of infrared energy that have been transmitted in a common path through a sample that has a component content to be determined, where the component may be carbon dioxide or methane or water vapor, for example. The pulses are temporally spaced and include a first wavelength-dependent pulse having a given wavelength selected for strong absorption by the component, second and third wavelength-dependent pulses having a wavelength selected for weak absorption by the component and a fourth nominal pulse having a reference intensity. The duration of the nominal fourth pulse equals the entire time that elapses between the end of a wavelength-dependent pulse and the start of the next succeeding wavelength-dependent pulse. The intensity of the nominal fourth pulse has zero departure from the reference intensity. Comparison of the wavelength-dependent pulses with the reference intensity is facilitated by considering that reference intensity as if it were a pulse of zero amplitude occurring at the mid-point of the elapsed time between successive wavelength-dependent pulses. For simplicity, the nominal fourth pulse is referred to below as the fourth pulse and a background or reference, nominal pulse that is referred to as a background or reference pulse. The relative order of such temporally spaced first through fourth pulses is selected such that the second pulse temporally precedes, and the third pulse temporally follows, the first pulse. In response to the first pulse, the sensor generates a first sensor pulse (N1) having a value related to the amount of the component in the sample. In response to the second and third pulses, the sensor generates second and third sensor pulses (N2 and N3) having values relatively weakly affected by the amount of the component in the sample. In response to the fourth pulse, the sensor generates a fourth sensor pulse (N4) having a value related to the background radiation incident on the sensor. The concentration of the component in the sample is determined by the following transmissivity ratio:

$$\frac{N1 - N4}{[K2(N2 - N4) + K3(N3 - N4)]},$$

where K2 and K3 sum to 1.00 and are chosen to yield a time-weighted average of the sensor pulses N2 and N3 that is applicable at the time of the sensor pulse N1.

In the method of the present invention applied to measuring water vapor concentration in a sample, a beam of infrared energy is generated in the form of separate pulses, where a first pulse is strongly absorbed by water vapor and second and third pulses on either side of the first pulse are weakly absorbed by water vapor. The second and third pulses are at a wavelength in a weak water vapor absorption region centered at about 2.5 microns, and the first pulse is at a wavelength in a strong water vapor absorption band centered at about 2.6 microns. The first, second and third pulses are temporally spaced such that one of such second and third pulses occurs at some time before, and another occurs at some time after, the first pulse. A fourth reference pulse related to the background radiation is interposed among the first, second and third pulses. The pulses are sensed by an indium arsenide sensor that successively converts the pulses to separate sensor pulses having values N1, N2, N3 and N4 related to the amount of infrared energy in such respective first, second, third and fourth pulses received by the sensor. The moisture content of the sample is indicated by the above transmissivity ratio.

With these and other objects in mind, the present apparatus and method of determining the concentration of individual components of a multi-component system includes a source of electromagnetic radiation for directing an electromagnetic radiation beam through a sample that has a component content to be determined. The electromagnetic radiation beam includes a selected wavelength band that is strongly absorbed by the component. A photovoltaic sensor is responsive to such beam after transmission thereof through the sample of the multi-component system for generating an output signal indicative of the concentration of such component in the system. The photovoltaic sensor is responsive to the electromagnetic radiation and provides a linear output over a relatively wide range of intensity of the electromagnetic radiation.

When the apparatus of the present invention is a hygrometer, it may include an infrared source for producing a broadband infrared energy beam that includes a selected strong water vapor absorption band and a weak water vapor absorption region. The broadband energy beam is chopped to select a series of infrared pulses, including a temporally first pulse having a wavelength in the weak absorption region, a temporally second pulse having a wavelength in the strong band and a temporally third pulse having a wavelength in the weak absorption region. A fourth reference pulse representing background radiation is interposed in such series of chopped pulses. The first through fourth infrared pulses are in a pre-determined temporal order and are transmitted in a given path across a volume of the sample. An indium arsenide infrared sensor is responsive to the first through fourth pulses exiting from the sample for generating an output signal in proportion to the transmissivity ratio:

$$\frac{N1 - N4}{[K2(N2 - N4) + K3(N3 - N4)]},$$

where N1, N2 and N3 are proportional to the transmission through the sample of the respective first pulse, second pulse and third pulse; N4 is proportional to the transmission of the background radiation through such sample and to other offsets of the detector; and K2 and K3 sum to 1.00 and are chosen to yield a time-weighted average of said pulses N2 and N3 that is applicable at the time of the pulse N1; with the reference pulse N4 being subtracted in each case to render the ratio independent of variations in the background radiation and the baseline reference of the sensor.

BRIEF DESCRIPTION OF THE DRAWINGS

Other objects, features and advantages of the present invention will be apparent from examination of the following detailed descriptions which include the attached drawings, in which:

FIG. 1 is a schematic diagram of an apparatus constructed according to the principles of the present invention for measuring the concentration of individual components of a multi-component system, which apparatus is shown including an infrared source generating a beam of electromagnetic radiation that is chopped and directed through a sample and back into the housing for sensing by an electromagnetic radiation sensor;

FIG. 2A is a front elevational view taken along lines 2—2 in FIG. 1 showing one embodiment of a multiple wavelength light chopper having three filters for transmitting separate pulses of electromagnetic radiation having wavelengths related to a first component to be measured;

FIG. 2B is a view similar to that of FIG. 2A, but showing a second embodiment of a multiple wavelength light chopper having five filters for transmitting separate pulses of electromagnetic radiation including two pairs of multiple wavelengths related to two different components to be measured;

FIG. 3 is a schematic diagram showing the electromagnetic radiation detector connected to a voltage controlled oscillator that drives a cycle counter connected to a microprocessor that outputs a signal that indicates the concentration of individual components of a multi-component system;

FIGS. 4A through 4F are graphs, wherein FIG. 4A shows an original series of electromagnetic radiation pulses output using the chopper of FIG. 2A;

FIG. 4B shows attenuation of certain ones of the pulses according to the concentration of an individual component of the multi-component system;

FIG. 4C shows voltage output pulses from the sensor;

FIG. 4D shows a stylized representation of outputs that represent the totalized number of counts of high frequency pulses generated by the voltage controlled oscillator in response to the voltage output pulses from the sensor when integrated over the respective time periods corresponding to each voltage output pulse shown in FIG. 4C;

FIG. 4E shows a series of electromagnetic radiation pulses output using the chopper shown in FIG. 2B;

FIG. 4F is similar to FIG. 4D but shows outputs that represent the number of counts of high frequency pulses generated in response to the pulses shown in FIG. 4E; and FIG. 5 is a perspective view of a commercial embodiment of the apparatus of the present invention.

DETAILED DESCRIPTION OF THE PREFERRED EMBODIMENTS

Absorption Characteristics

Referring to FIG. 1, the principles of the present invention are illustrated by an apparatus 10 for measuring the concentration of individual components of a multi-component system. Multi-component systems may be composed of, for example, air plus other gaseous components, such as carbon dioxide, methane, or water vapor. The apparatus 10 utilizes the characteristic that a particular one of such components strongly absorbs electromagnetic radiation that is within a specified band of wavelengths. Further, such particular component also relatively weakly absorbs electromagnetic radiation that is within a different region of wavelengths. For example, with respect to electromagnetic radiation in the infrared portion of the spectrum, a strong water vapor absorption band is centered at about 2.6 microns and a weak water vapor absorption region is centered at about 2.5 microns. With respect to other components of a multi-component system, methane has a strong absorption band centered at about 3.32 microns, and a weak absorption region centered at about 3.10 microns.

In the following description of the apparatus 10 and the method of the present invention, the strong absorption bands are referred to as the "strong band B1" and the preferred wavelength within the strong band is referred to as "lambda 1", where the preferred wavelengths for various components are as follows:

Chart I

| | Strong Absorption | |
|---|---|---|
| Designation | Component | Preferred Wavelength (microns) |
| lambda 1C | $CO_2$ | 2.780 |
| lambda 1M | methane | 3.316 |
| lambda 1W | water vapor | 2.595 |

Similarly, the weak absorption bands are referred to generally as the "weak region B2" and the preferred wavelength within the weak absorption region is referred to as "lambda 2", where:

Chart II

| | Weak Absorption | |
|---|---|---|
| Designation | Component | Preferred Wavelength (microns) |
| lambda 2C | $CO_2$ | 2.900 |
| lambda 2M | methane | 3.100 |
| lambda 2W | water vapor | 2.500 |

General Description of Apparatus 10

Referring in more detail to FIG. 1, the apparatus 10 for measuring the concentration of individual components of a multi-component system or sample 11 is shown. The apparatus 10 includes a housing 12 having a sealed section 13 and a section 14 that is open to permit the sample 11 to flow therein for sampling. The housing 12 is shown having a pair of windows 15 and 15' that are transparent to electromagnetic radiation. The sealed section 13 of the housing 12 contains a source 16 of electromagnetic radiation that produces a broadband electromagnetic radiation signal 17 in the form of a unitary beam 18. The beam 18 includes the strong absorption band B1 and the weak absorption region B2 for the component. A chopper 19 selects from the broadband signal 17 a series 20 of separate electromagnetic radiation pulses to form a chopped beam 18'. The pulses are shown in FIGS. 4A, 4B and 4E as having a Gaussian distribution. The chopped beam 18' includes (see FIG. 4A) a pulse 21A having the wavelength lambda 2 within the weak absorption region B2. The series 20 also includes a pulse 22B having the wavelength lambda 1 within the strong absorption band B1 and a pulse 21D having the wavelength lambda 1 within the weak absorption region B2. Background electromagnetic radiation 17' is shown superimposed on the beam 18' after the chopper 19 forms the pulses 21A, 22B and 21D, such that each pulse 21A, 22B and 21D has some value resulting from the background electromagnetic radiation 17'. That value is referred to as a background or reference, nominal pulse 23C. Also, when the broadband electromagnetic radiation beam 18 is completely blocked (such that there is no pulse 21A, 22B or 21D), the background electromagnetic radiation 17' will still be transmitted out of the window 15 and is shown as the pulse 23C.

The chopper 19 is designed so that the pulses 21A, 22B and 21D are formed in a predetermined temporal order. The timing of the pulses 21A, 22B and 21D is indicated by the letters "A", "B", etc., such that the predetermined order shown as an example in FIGS. 4A and 4B for the series 20 of pulses is the temporally first pulse 21A followed by the temporally second pulse 22B, followed by the temporally third pulse 21D. The background nominal pulse 23C is shown interspersed in the series 20 of pulses.

The series 20 of pulses 21A, 22B and 21D and the reference pulse 23C are transmitted out of the window 15 and through the open section 14 in a known path 24 having a selected length L. The pulses 21A, 22B, 23C and 21D reflect off a mirror 25 and are transmitted through the window 15' onto a detector or sensor 26. According to the component concentration of the sample 11 that is in the open section 14, the pulses 22B that are within the strong absorption band B1 are absorbed by the component in the open section 14. In FIG. 4B, the transmitted pulses 21A, 22B, 23C and 21D are shown after exiting from the sample 11 as the respective pulses 21A', 22B', 23C' and 21D'. The intensity of the pulse 22B' after absorption to some degree is less than that of the pulses 21A' and 21D' that are within the weak absorption region B2. The detector 26 is responsive to the series 20 of pulses and to the reference pulse 23C'. The detector 26 generates a series of sensor pulses 27, 28, 29 and 30 (FIGS. 3 and 4C) in response to the series 20 of pulses and the reference pulse 23C'. In response to the respective sensor pulses 27, 28, 29 and 30, a voltage controlled oscillator 31 generates high frequency signals 32, 33, 34 and 35 (FIG. 3). The number of cycles in each such respective high frequency signal 32, 33, 34 and 35 is counted by a counter 36 and the number of counts N1, N2, N3 and N4 of high frequency pulses in the respective signals 32, 33, 34 and 35 are stored in a microprocessor 37.

In the simplest case, when no consideration is given to the background pulse 23C nor the corresponding count N3, the pulses 21A and 21D are temporally related so that they are spaced from the pulse 22B by equal numbers of time intervals. In this case, the microprocessor 37 obtains the following transmissivity ratio and generates an output signal 38 that indicates the concentration of the component of the multi-component system:

$$\frac{N2}{(N1 + N4)(0.5)}. \quad (1)$$

For greater accuracy, variations in the background signal 17' may be taken into consideration by obtaining the following transmissivity ratio:

$$\frac{N2 - N3}{[K_i(N1 - N3) + K_i(N4 - N3)]}, \quad (2)$$

where $K_i$ are constants having values 1 through n according to the number of time intervals in the temporal spacing of the sensor pulse with which it is related relative to the sensor pulse corresponding to the pulse of the chopped beam 18' that is within the strong absorption band B1, such that the denominator of the transmissivity ratio (2) could also be expressed as:

$$[K1(N1-N3)+K4(N4-N3)],$$

and where K1 and K4 sum to 1.00 and are chosen to yield a time-weighted average of the sensor pulses N1 and N4 that is applicable at the time of the sensor pulse N2.

General Description of Method

Still referring to FIG. 1, the method of measuring the concentration of individual components of a multi-component system or sample 11 according to the principles of the present invention includes the steps of generating the unitary beam 18 of electromagnetic radiation and then forming the separate pulses 21A, 22B and 21D of the chopped beam 18'. With the pulses 21A, 22B and 21D temporally sequenced, for example as shown in FIG. 4A, the temporally first and fourth pulses 21A and 21D respectively are at the particular wavelength lambda 2 in the weak absorption region B2. The temporally second pulse 22B is at the wavelength lambda 1 in the strong absorption band B1.

The pulses 21A, 22B and 21D are transmitted across the sample 11 in the path 24 that is folded at the mirror 25. The temporally third reference pulse 23C is interspersed and transmitted in the folded path 24. The sample 11 variably absorbs the electromagnetic radiation in the second pulse 22B according to the concentration of the component in the sample 11. The method further includes the steps of using the detector 26 to successively convert the first, second and fourth pulses 21A', 22B' and 21D' respectively to the separate sensor pulses 27, 29 and 30 respectively, and to convert the reference pulse 23C' to the sensor pulse 28. The values over time of each respective first, second, third and fourth sensor pulses 27, 28, 29 and 30 are represented by the respective counts N1, N2, N3 and N4 and transmissivity ratios (1) or (2) are processed to generate the output 38 (FIG. 3) indicative of the concentration of an individual component of the multi-component system.

Detailed Description of Apparatus 10

Referring in detail to FIGS. 1 and 5, the apparatus 10 of the present invention for measuring the concentration of individual components of a multi-component system or sample 11 includes the housing 12 shown as an enclosure for completely containing the active elements of the apparatus 10 and separating them from the sampled gas volume, which may be contaminated, for example. The housing 12 is hermetically sealed to form the sealed section 13 that keeps the environment and such contamination out of the active elements of the apparatus 10.

The housing 12 also includes the open section 14 for supporting the mirror 25. While the open section 14 can be open to the atmosphere as in FIG. 1, in FIG. 5 the open section 14 is shown being defined by a conduit 14' that may be part of the gas coolant system of a gas-cooled nuclear reactor (not shown), for example. In the preferred embodiment of the invention shown in FIG. 5, arms 39—39 extend from the sealed section 13 of the housing 12 around the conduit 14' to support the mirror 25 in a desired location relative to both the electromagnetic radiation source 16 and the detector 26 (FIG. 1). Windows 40 (shown in dashed lines) and 41 are provided in the opposite sides of the conduit 14' to permit the chopped beam 18' to be transmitted through the sample 11. The arms 39—39 support the mirror 25 relative to the sealed section 13 so that the length L of the path 24 through which the chopped beam 18 is transmitted will be a selected value, such as 1.0 meter, measured from the window 15 to the mirror 25 to the window 15'.

In FIG. 1, the electromagnetic radiation source 16 is shown mounted in the sealed section 13 of the housing 12. The electromagnetic radiation source 16 generates the broadband electromagnetic radiation signal 17 in the form of the unitary beam 18. When the components of the multi-component system or sample 11 are carbon dioxide, methane or water vapor, for example, the electromagnetic radiation source 16 may be a tungsten filament-type of source that generates the beam 18 in the infrared portion of the spectrum. Such infrared broadband signal 17 thus includes the strong band B1 and the weak region B2 for the components shown in Charts I and II above.

For purposes of describing first and second preferred embodiments of the present invention, the broadband signal 17 is described as including the strong water absorption band B1W, the weak water absorption region B2W, the strong methane absorption band B1M and the weak methane absorption region B2M. Referring to FIG. 1, such broadband signal 17 is emitted from the source 16. A collimating lens 42 forms the broadband signal 17 into parallel rays that form the collimated unitary beam 18.

The chopper 19 includes a motor 43 having a shaft 44. In a first embodiment of the chopper 19, the shaft 44 carries a chopper disk 45 (FIG. 2A). The chopper disk 45 is shown including a first filter section 46 that transmits only the wavelength portion of the unitary beam 18 for weak water vapor absorption (lambda 2W listed in Chart II). A second filter section 47 transmits only the wavelength portion for strong water vapor absorption (lambda 1W listed in Chart I). In this embodiment, a third filter section 48 is an opaque filter that does not transmit any of the unitary beam 18. The filter sections 46 and 47 have a band width of 0.5% relative to the preferred wavelengths listed in Charts I and II. Portions 49 of the chopper disk 45 are between and support the filter sections 46, 47, and 48. With the lens 42 adjacent the chopper disk 45 (FIG. 1), as the motor 48 rotates the chopper disk 45, the unitary beam 18 is formed into the chopped beam 18'. Still referring to FIG. 1A, a marker 50 on the chopper disk 45 cooperates with a stationary position detector 51 to indicate the location of the filters 46, 47 and 48 during each revolution of the chopper disk 45.

Referring to FIGS. 4A through 4F, various pulses and signals are shown. To indicate the temporal relationship of such pulses and signals, time t=0 is at the left and time increases from A to B to C, etc. In FIG. 4A the chopped beam 18' is shown including the first pulse 21A (at time interval A and at wavelength lambda 2W). Such pulse 21A is followed by the pulse 22B (at time interval B and at wavelength lambda 1W) and by the background or reference signal 17' that is superimposed on the chopped beam 18'. The reference signal 17' is shown as the background or reference pulse 23C for simplifying the description. It is to be understood, however, that when the portions 49—49 block the beam 18, the background radiation 17' enters the path 24 and forms the background level of radiation of the chopped beam 18'. This completes the electromagnetic radiation pulses of the chopped beam 18' and the background radiation signal 17' that occur when the chopper disk 45 rotates through one revolution. As the chopper disk 45 rotates through another revolution, the pulse 21D (at time interval D and wavelength lambda 2W) is next, followed by the pulse 22E (at time interval E and wavelength lambda 1W), the reference pulse 23F and the pulse 21G (at time interval G and wavelength lambda 2W). When the pulses 21, 22 and 23 are referred to without the time interval letters "A", "B", etc., such reference is unrelated to the timing of the pulse 21, 22 or 23 to which reference is made.

As shown in FIG. 4A, there is a signal 21 at the weakly absorbed wavelength lambda 2W that temporally precedes and one that follows the signal 22 that is at the strongly absorbed wavelength lambda 1W. The relative timing of the pulses 21 and 22, or the temporal sequence thereof, is based on how the filter sections 46, 47 and 48 are arranged on the chopper disk 45. The arrangement shown in FIG. 2A results in the temporal sequence of pulses 21A, 22B, 21D, 22E and 21G, with the reference pulses 23C and 23F interspersed. Other arrangements of the filter sections 46, 47 and 48 will result in a different temporal sequence of the pulses 21, 22 and 23, but when any group 52 of pulses is considered, one such signal 21 will temporally precede and one will temporally follow the signal 22, with pulse 23 being interspersed among the pulses 21 and 22. While FIG. 4A shows the pulse 21A temporally preceding (and next to) the pulse 22B, the term "temporally preceding" and variations thereof include the pulse 21A preceding the pulse 22B by more than one time interval. Similarly, while the pulse 21D is shown in FIG. 4A temporally following the pulse 22B by more than one time interval, the pulse 21D could be the next pulse temporally following the pulse 22B.

Referring to FIG. 2B, a second preferred embodiment of the chopper 19 is shown including a chopper disk 53 having the three filter sections 46, 47 and 48, plus two additional filter sections 54 and 55. The filter section 54 may, for example, transmit only the weak absorption wavelength lambda 2M for methane and the filter section 55 the strong absorption wavelength lambda 1M for methane.

When the chopper disk 53 rotates, as shown in FIG. 4E the pulses 21A, 22B and 23C will be followed by a fifth pulse 56D (at time interval D and at wavelength lambda 2M) and by a sixth pulse 57E (at time interval E and wavelength lambda 1M). The temporal preceding and following relationship between pulses 21 and 22 appears in the form of the pulses 21A and 21F relative to the pulse 22B. Similarly, such relationship appears in the form of the pulses 56D and 56I relative to the pulse 57E. The reference pulses 23C and 23H are interspersed, here at every fifth pulse as shown in FIG. 4E.

Referring again to FIG. 1, a main centerline 58 is shown extending perpendicularly from the center of the mirror 25 to and through the housing 12. The chopped beam 18' that is transmitted from the lens 42 extends along an outbound centerline 59 at an angle 60 relative to the main centerline 58. The outbound centerline 59 of the outbound chopped beam 18' intersects the center of the mirror 25. The source 16 and the lens 42 are mounted so that the broadband beam 18 and the chopped beam 18' extend along the path 24 centered along the outbound centerline 59. The shaft 44 mounts the chopper disk 45 so that it is perpendicular to the outbound centerline 59 of the chopped beam 18'. As a result, the chopped beam 18' is transmitted in the outbound direction onto the center of the mirror 25.

The chopped beam 18', along with the background radiation signal 17' from external heat sources and the housing 12, is reflected off the mirror 25 and returns along an inbound centerline 61 that is also at the angle 60 relative to the main center line 58. The chopped beam 18' is thus folded and transmitted along the length L of one meter in the folded path 24 from the window 15 to the mirror 25 to the window 15'.

Considering the component as being water vapor and the use of the chopper disk 45 having the filter sections 46, 47 and 48, as the chopped beam 18 and the internal and external background radiation signal 17' are transmitted across the folded path 24, only the pulses 22B and 22E at the wavelength lambda 1W in the strong band B1 are attenuated by the water vapor component in the sample 11. For the chopper disk 45 shown in FIG. 2A, such attenuation is shown in FIG. 4B, where the amplitudes of the pulses 21A' and 21D' arriving at the detector 26 are at or close to their original amplitudes, whereas the pulses 22B' and 22E' are shown having smaller amplitudes due to the attenuation by the absorbing water vapor component in the sample 11. The attenuation of the pulses 22B' and 22E' is shown unequal in FIG. 4B, to illustrate that the actual attenuation of a given pulse 22 depends upon the amount of the absorbing component in the sample 11 at the time interval during which the pulse 22 is transmitted across the sample 11. In practice, since the sample 11 may be very variable and may flow through the open section 14 rapidly, the chopper disk 45 is rotated at about 1200 rpm so that the amplitude of the pulses 22 will not change substantially from pulse to pulse, such as from the pulse 22B' to the pulse 22E'.

As indicated, both the chopped, folded beam 18' and the background radiation signal 17' from internal sources and external sources are transmitted through both of the windows 15 and 15' prior to reaching the detector 26. During episodes of rain or snow, water droplets or snowflakes can partially obscure the windows 15 and 15'. Considering the chopped beam 18 resulting from the chopper disk 45 and including the strong and weak water vapor regions B1W and B2W, the partial obscuration of the windows 15 and 15' is effective to attenuate the pulses 22 at wavelength lambda 1W at which strong water vapor absorption takes place. Such obscuration also attenuates the pulses 21 at wavelength lambda 2W where little or no water vapor absorption takes place. By selecting the wavelengths lambda 2W and lambda 1W that are close together in the absorption spectrum (as shown in Charts I and II), the attenuation effect of such water droplets or snowflakes on the windows 15 and 15' will be effectively comparable on such pulses 21, 22 and 23. As discussed below, since the ratio of intensities of such pulses 21, 22 and 23 does not vary with varying percentages of attenuation due to such water droplets or snowflakes, a reliable determination of the vapor density in the sample 11 can be obtained. The unchopped background infrared radiation signal 17' is also subject to attenuation by the partially obscured windows 15 and 15'. The effect of this attenuation is a change in the direct current bias point of the detector 26. This corresponds to the value of a base or reference line 62 shown in FIG. 4C to which the pulses 27, 28, 29 and 30, for example, are referenced. Depending upon the amount of attenuation of such unchopped radiation signal 17', the value of the direct current bias point, and hence the reference line 62, will vary. Since the concentration of the component in the multi-component system is indicated by the transmissivity ratios (1) and (2), such variation of the reference line 62 does not have any effect on the value of the concentration.

As shown in FIG. 1, the chopped, folded beam 18' and the unchopped background radiation signal 17' are transmitted through the window 15, into the sealed section 13 and through a lens 63 that focuses the chopped beam 18' and the unchopped radiation signal 17' onto a sensor 64 of the detector 26. The sensor 64 is fabricated from indium arsenide and has a square sensing spot one millimeter on a side. The sensor 64 is packaged in a standard TO-8 package. An indium arsenide sensor 64 having the following characteristics has been found suitable for use according to the principles of the present invention when the apparatus 10 is, for example, a hygrometer for measuring water vapor concentration or an instrument for measuring methane concentration.

Chart III

Characteristics of Indium Arsenide Sensor 64

| CHARACTERISTIC | VALUE |
| --- | --- |
| Dynamic Impedance | 3–20 K Ohms |
| Time Constant | 1 microsecond |
| Peak Detectivity | $8 \times 10^{10}$ cm. (hertz)$^{+\frac{1}{2}}$ w$^{-1}$ |
| Operating Temperature | 200° K. |
| Peak Wavelength | 3.4 microns |
| Range of Sensitivity | 1–3.8 microns |
| Linearity | Linear over sensitivity range. |

The indium arsenide sensor 64 responds to the chopped pulse 18' and to the unchopped background radiation signal 17' and generates the voltage pulses 27, 28 and 29 shown in FIG. 4C for each revolution of the chopper disk 45. These voltage pulses 27 through 29 are referenced to the value of the reference line 62 shown in FIG. 4C. It is observed that the shapes of the sensor pulses 27 through 29 correspond to that of the sensed pulses 21A', 22B' and 23C' shown in FIG. 4B. During the next revolution of the chopper disk 45, the sensor 64 responds to the pulses 21D', 22E' and 23F' and generates sensor pulses 30, 66 and 67.

Referring now to FIG. 3, the detector 26 is shown in schematic form with the indium arsenide sensor 64. A sensor or voltage signal 68 is formed from the pulses 27 through 30, 66 and 67 that are generated in response to the pulses 21, 22 and 23 of the series 20 of electromagnetic radiation pulses in the chopped beam 18'. For purposes of illustration, the description of the sensor signal 68 is limited to the sensor pulses 27 through 30 that are generated in response to one of the groups 52 (FIG. 4A) of temporally related electromagnetic radiation pulses. The temporal relationship of the pulses 21A', 22B', 23C' and 21D' in the group 52 is such that the pulse 22B' is temporally preceded by the pulse 21A' and is temporally followed by the pulse 21D'.

The pulses 27 through 30 of the voltage signal 68 are applied to the voltage controlled oscillator 31. The oscillator 31 responds to the voltage signal 68 and generates the high frequency signals 32 through 35 in the frequency range up to one megahertz. The frequency of each such high frequency pulse 32 through 35 at any instant of time is proportional to the voltage of the corresponding voltage signal 27 through 30 at that instant of time. Thus, each high frequency pulse 32 through 35 includes a total number (or count) of cycles N that is proportional to the shape of the voltage pulse 27 through 30 to which it corresponds. For example, the number of cycles N1 corresponds to the number of cycles in the high frequency pulse 32, and N2 corresponds to the number of cycles in the pulse 33, N3 corresponds to the number of cycles in the pulse 34 and N4 corresponds to the number of cycles in the pulse 34. The high frequency signals are referred to generally by the reference number 69 and are applied to the counter 36. The counter 36 is triggered each time one of the markers 50 passes the position detector 51 so that the counter 36 is effective to count the number N of cycles in each separate high frequency pulse 32 through 35, for example. These numbers of cycles N1, N2, N3 and N4 for the respective pulses 32, 33, 34 and 35 correspond to the values N1, N2, N3 and N4 noted above in respect to the transmissivity ratio (1). Also, the value N3 corresponds to "N3" in the transmissivity ratio (2) above. The counts or numbers of cycles N are represented by counter pulses 70 that form a counter signal 71. For ease of reference (FIG. 4D), counter pulses 70A, 70B, 70C and 70D relate to the time intervals A, B, C and D used to identify the radiation pulses 21A, 22B, 23C and 21D of the group 52 of pulses shown in FIG. 4A. The counter signal 71 is applied to the microprocessor 37 that is programmed in a standard manner for calculating the transmissivity ratios (1) and (2) with respect to each group 52 of sensor pulses 21, 22 and 23. In particular, as each counter pulse 70A, 70B, 70C and 70D is received by the microprocessor 37 from the counter 36, the count values of N1, N2, N3 and N3 are stored. When all of the pulses 70A, 70B, 70C and 70D have been received and the values of N1, N2, N3 and N4 stored, the microprocessor 37 is effective to calculate the transmissivity ratio (1). This is done by obtaining the sum of N1 and N4 and multiplying it by 0.5 to obtain the denominator of the transmissivity ratio (1). The denominator is divided into the value of N2 (or the decimal value of the denominator is multiplied by the value of N2) to obtain the output 38 that may be displayed on a digital display 72 of the microprocessor 37 to represent the water vapor content of the sample 11. This represents the absolute humidity of the sample volume 11.

Referring to FIGS. 4A and 4B, since the background radiation 17' is superimposed on the chopped beam 18', at each time interval C, F, etc. at which the chopper wheel 19 positions the opaque section 48 in front of the source 16, the only radiation of the chopped beam 18' will be that of the background radiation 17'. Thus, the values of the radiation pulses 23C, 23F, etc. indicate how much of the values of the pulses 21A and 22B, for example, are caused by the background radiation 17'. For those situations in which the background radiation level is known to be relatively constant, the transmissivity ratio (1) may be used. For those situations in which the level of background radiation over time is not known, the transmissivity ratio (2) should be used. In a similar manner, when the chopper disk 53 is used, revolutions thereof will result in the electromagnetic radiation pulses 21A, 22B, 23C, 56D, 57E, 21F, 22G, 23H, etc. as shown in FIG. 4E. In a manner similar to that described above with respect to the processing of the electromagnetic radiation pulses in the group 52, the electromagnetic radiation pulses shown in FIG. 4E are processed for measuring the concentration of two components of the multi-component system or sample 11, where the components are water vapor and methane. Thus, counts N5 through N14 are obtained and correspond to the respective electromagnetic radiation pulses 21A, 22B, 23C, 56D, 57E, 21F, 22G, 23H, 56I and 57J.

Since the counts N5 through N14 do not represent the simplest case to which the transmissivity ratio (1) is applicable, the transmissivity ratio (2) for water vapor is used instead and would be expressed as follows:

$$\frac{N6 - N7}{[K_i(N5 - N7) + K_i(N10 - N7)]} \quad (3)$$

After substituting for $K_i$ as indicated above, the transmissivity ratio (3) is expressed as:

$$\frac{N6 - N7}{[K5(N5 - N7) + K10(N10 - N7)]}, \quad (4)$$

where K5 and K10 correspond respectively to K1 and K4 discussed with respect to the transmissivity ratio (2).

With respect to methane, since the counts N5 through N14 do not represent the simplest case to which the transmissivity ratio (1) is applicable, the transmissivity ratio (2) is used instead and would be expressed as follows:

$$\frac{N9 - N12}{[K_i(N8 - N12) + K_i(N13 - N12)]} \quad (5)$$

After substituting for $K_i$ as indicated above, the transmissivity ratio (5) is expressed as:

$$\frac{N9 - N12}{[K8(N8 - N12) + K13(N13 - N12)]}, \quad (6)$$

where K8 and K13 correspond respectively to K1 and K4 discussed with respect to the transmissivity ratio (2).

For even more accuracy, the reference or background cycle count that is substracted from each cycle count N5, N6, and N10 (for example) should be that cycle count that is temporally the closest to the respective value N5, N6, or N10. Thus, the transmissivity ratio (4) would be used in the form of:

$$\frac{N6 - N7}{[K5(N5 - N7) + K10(N10 - N12)]}, \quad (7)$$

where K5 and K10 correspond respectively to K1 and K4 in transmissivity ratio (2).

It should be understood that because the voltage signal 68 is linear with respect to the intensity of the sensed electromagnetic radiation over the operating range of 1.0 to 3.2 microns of the photovoltaic detector 26, the alternating voltage signal 68 from the detector 26 may be separated from a relatively strong DC signal (represented by the pulse 23C, for example) generated by the detector 26 in response to the background radiation 17'. Such separation effectively occurs in the microprocessor 37 when it calculates ratios (2), (4), (6) or (7) for generating the displayed concentration output 38. The linearity of the detector 26 in response to the electromagnetic radiaition beam 18' and to the background radiation 17' over a range of intensity makes it possible to indicate accurately the concentration of the related component using the transmissivity ratios (1) and (2), (4), (6) and (7). In particular, considering FIG. 4D as an example, since the counts N1 and N4 are based on the temporally spaced pulses 21A and 21D, only if the response of the detector 26 is linear with respect to the intensity variations that occur between the time intervals A and D, for example, will the required accuracies of the transmissivity ratio (2) be obtained. Such linearity assures that the various intensities of the pulses 21A and 21D, for example, received by the detector 26 will be accurately represented by the corresponding counts N1 and N4, rendering the transmissivity ratios (2), (4), (6) and (7) accurate even though the counts N1 and N4 are temporally spaced.

Since the circuitry shown in FIG. 3 is capable of separating the alternating signal 68 generated in response to the chopped pulses 21 and 22 from the background radiation 17', it is not necessary to control the temperature of the housing 12. Moreover, the temperature of the indium arsenide sensor 64 may also be left uncontrolled. On the other hand, if desired, the sensor 64 may be cooled by a standard thermoelectric cooler 73 to a selected temperature, such as 200° K. In an embodiment of the present invention in which such a sensor 64 was cooled, there was a power penalty of 1.0 watt. While such cooling of the sensor 64 provides an order of magnitude improvement in signal to noise ratio of the voltage signal 68 from the sensor 64, a hygrometer constructed in the manner of the apparatus 10 has been found to function satisfactorily without such cooling of the sensor 64.

Additional accuracy may be provided to the calculation of the transmissivity ratios (1) through (7) to indicate the component concentration. For example, when there are many counter pulses 70 as shown in FIG. 4F, four time intervals E, F, G and H separate the N8 counter pulse 70D from the N13 counter pulse 70I, and three time intervals (F, G and H) separate the N9 counter pulse 70E from the N13 count pulse 70I. The microprocessor 37 is programmed to interpolate the value of the reference pulses 23 at any given time interval. For example, if the reference radiation 17' varies linearly, the slope of the reference pulse 23 is derived from the N7 and the N12 counter pulses 70C and 70H. Multiplying the slope by the number of time intervals between the N12 counter pulse 70C and the counter pulse 70 which is being computed (time interval E, for example) yields a value of a reference count N corresponding to the reference pulse 23 at the time E. This is subtracted from N9 in computing the transmissivity ratio (6) instead of subtracting the N12 value that corresponds to the time interval H.

Similarly, the slope-based interpolation values of a reference count N at the time interval D and at the time interval I are used respectively in the transmissivity ratio (6) in the (N8−N12) and (N13−N12) calculations in place of the N12 value. In this manner, the reference count subtracted from the N8, N9 and N13 counts will be closer to the actual reference count that exists at the respective time intervals D, E and I.

The transmissivity ratios (2) through (7) include a denominator that represents the time-weighted average of the weak counter pulses 70 that are temporally on opposite sides of a strong counter pulse 70 (see FIG. 4F where counts N5 and N10 relate to the respective weak counter pulses 70A and 70F, for example). Thus, where the weak counts, such as N5 and N10, vary over time, for example, the selection of the constants $K_i$ accomplishes the time-weighted averaging so that the values for the weak counts in the denominator are time-averaged to the time interval B, for example.

If desired, a therometer 74 may be located adjacent the path 24 of the sample 11 for providing data necessary, for example, to convert the absolute humidity data to relative humidity data and other traditional humidity units such as dew point.

While the preferred embodiment has been described in order to illustrate the fundamental relationships of the present invention, it should be understood that numerous variations and modifications may be made to these embodiments without departing from the teachings and concepts of the present invention. Accordingly, it should be clearly understood that the form of the present invention described above and shown in the accompanying drawings is illustrative only and is not intended to limit the scope of the invention to less than that described in the following claims.

What is claimed is:

1. In an apparatus for measuring the concentration of individual components of a multi-component system, said apparatus being in the form of a hygrometer, wherein said multi-component system includes at least water vapor in the coolant-gas stream of a gas-cooled nuclear reactor, said apparatus including means for transmitting an electromagnetic radiation input signal through a sample that has at least one of said system components therein, said electromagnetic radiation input signal being within a broad wavelength band that includes a given wavelength selected for strong absorption by said one component in said sample; the improvement comprising:

means responsive to said electromagnetic radiation input signal after transmission thereof through said sample for generating an output signal indicative of the concentration of said one component in said sample, said generating means including means fabricated from indium arsenide and being linearly responsive to said transmitted electromagnetic radiation input signal at said given wavelength and over a relatively wide portion of said wavelength band of said input signal for generating said output signal, said indium arsenide generating means being positioned to respond to the electromagnetic radiation input signal after transmission through said coolant-gas stream and any water vapor therein.

2. In an apparatus for measuring the concentration of individual components of a multi-component system, wherein said system includes the component water vapor and said apparatus is a hygrometer including means for transmitting an electromagnetic radiation input signal through a sample that has at least the component water vapor therein, said electromagnetic radiation input signal being within a broad wavelength band that includes a given wavelength selected for strong absorption by said water vapor component in said sample; the improvement comprising:

means responsive to said electromagnetic radiation input signal after transmission thereof through said sample for generating an output signal indicative of the concentration of said water vapor component in said sample, said generating means including means fabricated from indium arsenide and being linearly responsive to said transmitted electromagnetic radiation input signal at said given wavelength and over a relatively wide portion of said wavelength band of said input signal for generating said output signal;

said generating means fabricated from indium arsenide having a range of sensitivity to said radiation input signal of from 1 to 3.8 microns and said linear response being over said range of sensitivity.

3. In an apparatus for measuring the concentration of individual components of a multi-component system, said apparatus being in the form of a hygrometer including means for transmitting an electromagnetic radiation input signal through a sample that has at least one of said system components therein, wherein said system includes water vapor as one of the individual components, said electromagnetic radiation input signal being within a broad wavelength band that includes a given wavelength selected for strong absorption by the water vapor in said sample; the improvement comprising:

means responsive to said electromagnetic radiation input signal after transmission thereof through said sample for generating an output signal indicative of the concentration of said one component in said sample, said generating means including means fabricated from indium arsenide and being linearly responsive to said transmitted electromagnetic radiation input signal at said given wavelength and over a relatively wide portion of said wavelength band of said input signal for generating said output signal;

said transmitting means including means for producing said electromagnetic radiation input signal in temporally spaced pulses, wherein one of said pulses has said given wavelength, and others of said pulses temporally precede and follow said one pulse and have a second wavelength selected for weak absorption by water vapor; and said indium arsenide means having a linear response to said electromagnetic radiation input signal at said given and second wavelengths over said relatively wide portion of said wavelength band of said input signal.

4. In an apparatus for measuring the concentration of individual components of a multicomponent system, including means for transmitting an electromagnetic radiation input signal through a sample that has at least one of said system components therein, said electromagnetic radiation input signal being within a broad wavelength band that includes a given wavelength selected for strong absorption by said one component in said sample; the improvement comprising;

means responsive to said electromagnetic radiation input signal after transmission thereof through said sample for generating an output signal indicative of the concentration of said one component in said sample, said generating means including photovoltaic means responsive to said transmitted electromagnetic radiation input signal at said given wavelength and linearly over a relatively wide range of input signal intensities for generating said output signal;

said transmitting means including means for producing said electromagnetic radiation input signal in temporally spaced pulses, wherein one of said pulses has said given wavelength, and others of said pulses temporally precede and follow said one pulse and have a second wavelength selected for weak absorption by said one component;

said photovoltaic means including an indium arsenide electromagnetic radiation detector having a linear response to said electromagnetic radiation input signal at said given and second wavelengths over a relatively wide range of intensity of said input signal; and said generating means generates said output signal based on the value of:

$$\frac{N2}{(N1 + N3)(0.5)},$$

where N1 is proportional to the transmission of one of said other pulses through said sample, N2 is proportional to the transmission of said one pulse through said sample, N3 is proportional to the transmission of another of said other pulses through said sample and said other pulses are temporally equally spaced from said one pulse.

5. In an apparatus for measuring the concentration of individual components of a multicomponent system, including means for transmitting an electromagnetic radiation input signal through a sample that has at least one of said system components therein, said electromagnetic radiation input signal being within a broad wavelength band that includes a given wavelength selected for strong absorption by said one component in said sample; the improvement comprising;

means responsive to said electromagnetic radiation input signal after transmission thereof through said sample for generating an output signal indicative of the concentration of said one component in said sample, said generating means including photovoltaic means responsive to said transmitted electromagnetic radiation input signal at said given wavelength and linearly over a relatively wide range of input signal intensities for generating said output signal;

said transmitting means including means for producing said electromagnetic radiation input signal in temporally spaced pulses, wherein one of said pulses has said given wavelength, and others of said pulses temporally precede and follow said one pulse and have a second wavelength selected for weak absorption by said one component;

said photovoltaic means including an indium arsenide electromagnetic radiation detector having a linear response to said electromagnetic radiation input signal at said given and second wavelengths over a relatively wide range of intensity of said input signal; and said photovoltaic means generates a signal N1 proportional to the transmission of one of said other pulses through said sample, a signal N2 proportional to the transmission of said one pulse through said sample, and a signal N3 proportional to the transmission of another of said other pulses through said sample; and said generating means generates said output signal based on the value of said signal N2 divided by the interpolated value of said N1 and N2 signals at the time of said N2 signal, said generating means being effective to obtain said interpolated value by interpolation using said N1 and N2 signals.

6. In an apparatus for measuring the concentration of individual components of a multicomponent system, including means for transmitting an electromagnetic radiation input signal through a sample that has at least one of said system components therein, said electromagnetic radiation input signal being within a broad wavelength band that includes a given wavelength selected for strong absorption of said one component in said sample; wherein a background electromagnetic signal is also detected by said photovoltaic means, the further improvement comprising:

means responsive to said electromagnetic radiation input signal after transmission thereof through said sample for generating an output signal indicative of the concentration of said one component in said sample, said generating means including photovoltaic means responsive to said transmitted electromagnetic radiation input signal at said given wavelength and linearly over a relatively wide range of input signal intensities for generating said output signal;

said transmitting means including means for producing said electromagnetic radiation input signal in temporally spaced pulses, wherein one of said pulses has said given wavelength, and others of said pulses temporally precede and follow said one pulse and have a second wavelength selected for weak absorption by said one component;

said photovoltaic means being responsive to said one and other pulses and to said background signal for respectively generating detector signals, wherein a detector signal N1A is the detector signal at time interval A and at said second wavelength, a detector signal N2B is the detector signal at time interval B and at said given wavelength, a detector signal NBC is the detector signal at time interval C and in response to said background signal, and a detector signal N1D is the detector signal N at time D and at said second wavelength; and said generating means generates said output signal based on the value of:

$$\frac{N2B - NBC}{[K1A(N1A - NBC) + K1D(N1D - NBC)]},$$

where K1A and K1D sum to 1.00 and are chosen to yield a time-weighted average of said signals N1A and N1D that is applicable at said time interval B.

7. In a hygrometer for measuring the concentration of water vapor as a component of a multi-component system, said hygrometer including means for transmitting an electromagnetic radiation input signal through a sample that has at least the water vapor as one of said system components therein, said signal being within a detector response wavelength band that includes a given wavelength selected for strong absorption by the water vapor in said sample; the improvement comprising:

means including a detector fabricated from indium arsenide for sensing electromagnetic radiation, said detector being responsive to said electromagnetic radiation input signal upon the exiting thereof from said sample and at said given wavelength for generating an output signal having a value that varies linearly with respect to the intensity of said electromagnetic radiation input signal transmitted through said sample at said given wavelength, said linearity being over an operating range of from 1 to 3.8 microns, where said given wavelength is in said operating range.

8. In a hygrometer for measuring the concentration of water vapor as a component of a multi-component system according to Claim 7, the further improvement comprising:

thermo-electric means for cooling said detector to improve the signal to noise ratio of said output signal.

9. In a hygrometer for measuring the concentration of water vapor as a component of a multi-component system according to Claim 7, the further improvement comprising:

said transmitting means including means for producing said electromagnetic radiation input signal in temporally spaced pulses, wherein one pulse having said given wavelength is preceded and followed by respective temporally preceding and temporally following pulses having a second wavelength in said detector response band, said second wavelength being selected for weak absorption by the water vapor;

said detector having said linear response to said pulses at said given and second wavelengths over the intensity range of said pulses; and said sensing means being responsive to said exiting electromagnetic radiation pulses for generating a series of said output signals.

10. In an apparatus for measuring the concentration of individual components of a multi-component system, said apparatus including means for transmitting an electromagnetic radiation input signal through a sample that has at least carbon dioxide or methane or water vapor as one of said system components therein, said signal being within a detector response wavelength band that includes a given wavelength selected for strong absorption by said one component in said sample; the improvement comprising;

said transmitting means including means for producing said electromagnetic radiation input signal in temporally spaced pulses, wherein one pulse having said given wavelength is preceded and followed by respective temporally preceding and temporally following pulses having a second wavelength in said detector response band, said second wavelength being selected for weak absorption by said one component;

means including a detector fabricated from indium arsenide for sensing electromagnetic radiation, said detector being responsive to said electromagnetic radiation input signal upon the exiting thereof from said sample and at said given wavelength for generating a series of output signals having a value that varies linearly with respect to the intensity of said electromagnetic radiation pulses at said given and second wavelengths transmitted through said sample, said linearity being over an operating range of from 1 to 3.8 microns, where said given and second wavelengths are in said operating range; and means are responsive to said series of output signals for producing a concentration measurement signal based on the value of:

$$\frac{N2}{(N1 + N3)(0.5)},$$

where N1 is the total value over time of a first output signal corresponding to said temporally preceding pulse, N2 is the total value over time of a second output signal corresponding to said one pulse having said given wavelength, N3 is the total value over time of a third output signal corresponding to said temporally following pulse and said first and third output signals are temporally equally spaced from said second output signal.

11. In an apparatus for measuring the concentration of individual components of a multi-component system, said apparatus including means for transmitting an electromagnetic radiation input signal through a sample that has at least carbon dioxide or methane or water vapor as one of said system components therein, said signal being within a detector response wavelength band that includes a given wavelength selected for strong absorption by said one component in said sample; the improvement comprising:

said transmitting means including means for producing said electromagnetic radiation input signal in temporally spaced pulses, wherein one pulse having said given wavelength is preceded and followed by respective temporally preceding and temporally following pulses having a second wavelength in said detector response band, said second wavelength being selected for weak absorption by said one component;

photovoltaic means including a detector fabricated from indium arsenide for sensing electromagnetic radiation, said detector being responsive to said electromagnetic radiation input signal pulses upon the exiting thereof from said sample and at said given and second wavelengths for generating a series of output signals having values linear with regard to the intensity of said electromagnetic radiation at said given and second wavelengths transmitted through said sample;

said detector having said linear response to said pulses at said given and second wavelengths over the intensity range of said pulses;

said detector is also responsive to background electromagnetic radiation transmitted through said sample for generating a reference signal NB that shifts the reference level of said output signals; and means to said series of output signals for producing said concentration measurement signal based on the value of:

$$\frac{N2 - NB}{[K1\,(N1 - NB) + K3\,(N3 - NB)]},$$

where N1 is the total value over time of a first output signal corresponding to said temporally preceding pulse, N2 is the total value over time of a second output signal corresponding to said one pulse having said given wavelength, N3 is the total value over time of a third output signal corresponding to said temporally following pulse, and K1 and K3 sum to 1.00 and are chosen to yield a time-weighted average of said signals N1 and N3 that is applicable at the time of the second output signal.

12. In a hygrometer, including means for transmitting an infrared signal through a sample that has a water vapor content to be determined, said infrared signal being within a detector response band that includes a given wavelength selected for strong absorption by water vapor in said sample; the improvement comprising:

a detector fabricated from indium arsenide, said detector being responsive to said infrared signal upon exiting thereof from said sample for generating an output signal having a value that varies linearly with respect to the intensity of said exiting signal at said given wavelength.

13. A hygrometer according to Claim 12, wherein: thermo-electric means are provided for cooling said detector to improve the signal to noise ratio of said output signal.

14. In a hygrometer according to Claim 12, the further improvement comprising:

said transmitting means including means for producing said infrared signal in the form of a series of pulses, wherein one of such pulses is at said given wavelength and others of said pulses temporally precede and follow said one such pulse and are at a second wavelength, said second wavelength being selected for weak water vapor absorption; and said detector has said linear response to said pulses at said given and second wavelengths with respect to the intensity of said pulses over the intensity range of said pulses, said detector being responsive to said pulses exiting said sample for generating a series of said output signals.

15. In a hygrometer according to Claim 12, wherein said detector response band is in the range of from 1 to 3.8 microns, the improvement further comprising:

said detector being effective to generate said output signal having a value that varies linearly with respect to the intensity of said exiting signal over said response band from 1 to 3.8 microns.

16. In a hygrometer including means for transmitting an infrared signal through a sample that has a water vapor content to be determined, said infrared signal being within a detector response band that includes a given wavelength selected for strong absorption by water vapor in said sample; the improvement comprising:

said transmitting means including means for producing said infrared signal in the form of a series of pulses, wherein one of such pulses is at said given wavelength and others of said pulses temporally precede and follow said one such pulse and are at a second wavelength, said second wavelength being selected for weak water vapor absorption;

means including a detector fabricated from indium arsenide, said detector being responsive to said pulses upon exiting thereof from said sample for generating a series of output signals having a value that varies linearly with respect to the intensity of said exiting pulses at said given and second wavelengths;

said detector having said linear response to said pulses at said given and second wavelengths with respect to the intensity of said pulses over a relatively wide range of intensities of said pulses; and means responsive to said series of output signals for producing a water vapor content signal based on the value of:

$$\frac{N2}{(N1 + N3)(0.5)},$$

where N1 is the total value over time of one of said output signals corresponding to said one of said preceding and following infrared pulses emitted from said sample, N2 is the total value over time of another of said output signals corresponding to said one infrared pulse at said given wavelength, N3 is the total value over time of another of said output signals corresponding to the other of said preceding and following infrared pulses at said second wavelength, and said preceding and following infrared pulses are temporally equally spaced from said one infrared pulse.

17. In a hygrometer including means for transmitting an infrared signal through a sample that has a water vapor content to be determined, said infrared signal being within a detector response band that includes a given wavelength selected for strong absorption by water vapor in said sample; the improvement comprising:

said transmitting means including means for producing said infrared signal in the form of a series of pulses, wherein one of such pulses is at said given wavelength and others of said pulses temporally precede and follow said one such pulse and are at a second wavelength, said second wavelength being selected for weak water vapor absorption;

means including a detector fabricated from indium arsenide, said detector being responsive to said pulses upon exiting thereof from said sample for generating a series of output signals having a value that varies linearly with respect to the intensity of said exiting pulses at said given and second wavelengths;

said detector having said linear response to said pulses at said given and second wavelengths with respect to the intensity of said pulses over a relatively wide range of intensities of said pulses; and said detector is responsive to background electromagnetic radiation transmitted through said sample for generating a reference signal NB that shifts the reference level of said output signals; and means responsive to said series of output signals for producing a water vapor content signal based on the value of:

$$\frac{N2 - NB}{[K1\,(N1 - NB) + K3\,(N3 - NB)]},$$

where N1 is the total value over time of one of said output signals corresponding to said one of said preceding and following infrared pulses emitted from said sample, N2 is the total value over time of another of said output signals corresponding to said one infrared pulse at said given wavelength, N3 is the total value over time of another of said output signals corresponding to the other of said preceding and following infrared pulses at said second wavelength, and K1 and K3 sum to 1.00 and are chosen to yield a time-weighted average of said signals N1 and N3 that is applicable at the time of the second output signal corresponding to said one infrared pulse.

18. In a hygrometer including means for transmitting an infrared signal through a sample that has a water vapor content to be determined, said infrared signal being within a detector response band that includes a given wavelength selected for strong absorption by water vapor in said sample; the improvement comprising:

said transmitting means including means for producing infrared signal in the form of a series of pulses, wherein one of such pulses is at said given wavelength and others of said pulses temporally precede and follow said one such pulse and are at a second wavelength, said second wavelength being selected for weak water vapor absorption;

means including a detector fabricated from indium arsenide, said detector being responsive to said infrared signal upon exiting thereof from said sample for generating a series of output signals having a value that varies linearly with respect to the intensity of said exiting signal at said given wavelength;

said detector having said linear response to said pulses at said given and second wavelengths with respect to the intensity of said pulses over a relatively wide range of intensities of said pulses;

said series of output signals generated by said detector including a signal N1 proportional to the transmission of one of said other pulses through said sample, a signal N2 proportional to the transmission of said one pulse through said sample, and a signal N3 proportional to the transmission of another of said other pulses through said sample; and means for producing a signal to indicate the water vapor concentration in said sample, said water vapor signal being based on the value of said signal N2 divided by the interpolated value of said N1 and N2 signals at the time of said N2 signal, said producing means being effective to obtain said interpolated value by interpolation using said N1 and N2 signals.

19. Apparatus for measuring the concentration of individual components of a multi-component system, including:

means for producing a broadband electromagnetic radiation input signal that includes a selected strongly absorbing band for one of said components therein and a selected weakly absorbing region for said one of said components;

means for selecting from said broadband input signal a series of electromagnetic radiation signals, said signals in said series including a first signal having a wavelength in said weakly absorbing region, a second signal having a wavelength in said strongly absorbing band and temporally spaced from said first signal, and a third signal having a wavelength in said weakly absorbing region and temporally spaced from said first and second signals, wherein said first, second and third signals are in a selected temporal order with said first and third signals temporally equally spaced from said second signal, said first, second and third signals being transmitted in a given path across a volume of said multi-component system;

a sensor fabricated from indium arsenide and being linearly responsive to the intensity of said first, second, and third selected signals upon exiting thereof from said multi-component system for generating respective first, second, and third outputs having respective total values N1, N2, and N3 over time proportional to the intensity of said respective first, second, and third signals transmitted through said multi-component system; and means responsive to said first, second, and third outputs for producing an output signal representative of the concentration of said individual component in said multi-component system, said output signal having a value that is proportional to:

$$\frac{N2}{(N1 + N3)\,(0.5)}.$$

20. Apparatus for measuring the concentration of individual components of a multi-component system, according to Claim 19, wherein:

said individual component is water vapor; and said strongly absorbing band is centered at about 2.6 microns and said weakly absorbing region is centered at about 2.5 microns.

21. Apparatus according to Claim 19, wherein:
said wavelength of said second signal is 2.595 microns and said wavelength of said first and third signals is 2.500 microns.

22. Apparatus according to Claim 19, wherein:
said selecting means is a chopper having filters for transmitting said first, second, and third signals in a pre-determined temporal sequence across said volume of said multi-component system.

23. Apparatus for measuring the concentration of individual components of a multi-component system according to Claim 19, wherein:
conduit means are provided for containing said system, said conduit means being in said given path of said input signal and having windows therein for permitting said input signal to be transmitted across the volume of said system contained in said conduit means; and
said system is a gaseous material for cooling a nuclear reactor.

24. Apparatus according to Claim 19, wherein:
said sensor is fabricated from indium arsenide for response to said first, second and third signals to generate said outputs in the form of a series of discrete output pulses;
said producing means includes a voltage controlled oscillator for response to said discrete output pulses for generating a high frequency signal corresponding to each said output pulse; and
said producing means further includes means for counting the number of cycles in each high frequency signal, such that said value N1 represents the number of cycles in a first high frequency signal representing said first signal, such that said value N2 represents the number of cycles in a second high frequency signal representing said second signal and such that said value N3 represents the number of cycles in a third high frequency signal representing said third signal.

25. Apparatus for measuring the concentration of individual components of a multi-component mixture, comprising:
sealed housing means for defining a volume separate from that of said multi-component mixture, said housing means having first and second windows therein;
means in said housing means for producing a broadband electromagnetic radiation beam that includes a selected strongly absorbing band for one of said components in said mixture, said beam of radiation also including a weakly absorbing region for said one of said components in said mixture;
chopping means for dividing said broadband beam into at least first, second and third electromagnetic radiation pulses, wherein said first and third radiation pulses are at a wavelength in said weakly absorbing region, said second pulse being at a wavelength in said strongly absorbing band; said first, second and third radiation pulses being temporally related according to a selected order;
means for directing said first, second, and third pulses in a common path through said first window, across said multi-component mixture and through said second window back into said housing;
said sealed housing means being effective to generate a fourth unchopped background electromagnetic radiation pulse;
an electromagnetic radiation sensor having a linear response with respect to sensed radiation intensity, said sensor being responsive to said first, second, third and fourth radiation pulses for producing first, second, third and fourth sensor pulses representing said respective first, second, third and fourth radiation pulses, said sensor pulses having a respective total value over time proportional to the respective amount N1, N2, N3 and N4 of each said respective first, second, third and fourth radiation pulses that is transmitted back into said housing means onto said sensor; and
means responsive to said sensor pulses for calculating the value of the difference between said amount N2 minus said amount N4, and dividing said difference by the value of said N1 and N3 amounts interpolated to the time interval over which said amount N2 is sensed, said dividing being done after subtracting from said value of said N1 and N3 amounts said N4 amount.

26. Apparatus according to Claim 25, wherein:
said value that is divided into said difference is obtained by interpolation using the average of said N1 and N3 amounts calculated as follows:

$$[(N1-N4)+(N3-N4)](0.5).$$

27. Apparatus according to Claim 25, for measuring the concentration of one of said components in the form of a gaseous nuclear reactor coolant material that is part of a multi-component nuclear reactor coolant mixture, wherein:
means are provided adjacent said sealed housing means for guiding said nuclear reactor coolant mixture through said common path, said guiding means having window means therein for allowing said first, second and third pulses to cross said mixture and return to said housing.

28. Apparatus according to Claim 25, wherein:
water vapor is an individual component of said mixture;
said one component is other than water vapor;
said broadband beam includes a selected strong water vapor absorption band centered at about 2.6 microns and a weak water vapor absorption region centered at about 2.5 microns;
said chopping means divides said broadband beam into fifth, sixth and seventh additional radiation pulses, wherein said sixth radiation pulse is at a wavelength in said strong water vapor absorption band and said fifth and seventh radiation pulses are at a wavelength in said weak water vapor absorption region;
said first through seventh radiation pulses are temporally related according to a selected order with said sixth pulse temporally centered between said fifth and seventh pulses;
said sensor is further responsive to said fifth, sixth and seventh radiation pulses for producing fifth, sixth and seventh sensor pulses, wherein said fifth, sixth and seventh pulses have a total value over time proportional to the respective amount N5, N6 and N7 of said respective fifth, sixth and seventh radiation pulses that are transmitted back into said housing means onto said sensor; and said calculating means also being effective to calculate the value of:

$$\frac{N6 - N4}{[(N5 - N4) + (N7 - N4)](0.5)}$$

to generate another output signal indicative of the water vapor content of said mixture.

29. A method of measuring the concentration of water vapor that forms a component of a multi-component system, comprising the steps of:

generating a beam of electromagnetic radiation in the form of separate pulses including first, second and third pulses, wherein said first and second pulses are in a wavelength band selected for weak absorption by said water vapor component, wherein said third pulse is in a wavelength region selected for strong absorption by said water vapor component, and wherein said wavelength bands and regions are within a range of from 1 to 3.8 microns, said first, second and third pulses being in a selected temporal order;

directing said pulses across a sample of said system to variably absorb said third pulse according to the concentration of said water vapor component in said sample; and using an indium arsenide detector to linearly with respect to radiation intensity at said strong and weak absorption wavelengths and successively convert said first, second and third pulses to separate output pulses to indicate the concentration of said water vapor component in said sample.

30. A method of measuring the concentration of an individual component of a multi-component system, comprising the steps of:

generating a beam of electromagnetic radiation in the form of separate pulses including first, second, third and fourth pulses, wherein said first and third pulses are in a wavelength region selected for weak absorption by said component and wherein said third pulse is in a wavelength band selected for strong absorption by said component, said fourth pulse is nominally of zero amplitude, said beam including background electromagnetic radiation super-imposed on said first, second, third and fourth pulses to vary the amplitude of all such pulses by the intensity of said background electromagnetic radiation, said pulses being temporally related such that one of said first and second pulses temporally precedes said third pulse and the other of said first and second pulses temporally follows said third pulse, the amounts of said temporal preceding and following being equal;

directing said first, second, third and fourth pulses across a sample of said system to variably absorb said third pulse according to the concentration of said component in said sample;

using an indium arsenide sensor to successively convert said first, second, third and fourth pulses to separate output pulses, wherein said output pulses have respective total values N1, N2, N3 and N4 over time and proportional to said respective first, second, third and fourth pulses that are transmitted back into said housing onto said sensor; and calculating the value of:

$$\frac{N3 - N4}{[(N1 - N4) + (N2 - N4)](0.5)}$$

to indicate the concentration of said component in said sample.

31. A method of indicating the water vapor content of a sample, comprising the steps of:

generating a beam of infrared energy in the form of separate pulses including first, second, and third infrared energy pulses, wherein said first and second pulses are at a wavelength in a weak water vapor absorption region centered at about 2.5 microns and said third pulse is at a wavelength in a strong water vapor absorption band centered at about 2.6 microns;

temporally relating said first, second, and third pulses such that one of said first and second pulses temporally precedes said third pulse and the other of said first and second pulses temporally follows said third pulse;

directing said infrared energy pulses across said sample to variably absorb said third pulse according to the water vapor content of said sample;

using an indium arsenide sensor to successively convert said temporally preceding, middle and following pulses to separate pulses A, B and C respectively wherein said pulses A, B and C have total values NA, NB, and NC over time proportional to the amplitude of each said respective pulses A, B and C that is transmitted back into said housing onto said sensor; and calculating the value of:

$$\frac{NB}{[KA(NA) + KC(NC)]}$$

to indicate the water vapor content of said sample, where KA and KC sum to 1.00 and are chosen to yield a time-weighted average of said values NA and NC that is applicable at the time of said pulse B.

32. A method of measuring the concentration of water vapor, comprising the steps of:

transmitting an electromagnetic radiation input signal through a sample that has at least water vapor therein, said electromagnetic radiation input signal being within a broad wavelength band that includes a given wavelength selected for strong absorption by water vapor in the sample; and using an indium arsenide detector to respond to said signal after transmission through said sample, said response being linear with respect to radiation intensity at said strong absorption wavelength and over a 1 to 3.8 micron band, and to convert the radiation intensity to an output signal to indicate the concentration of the water vapor in said sample.

* * * * *